(12) United States Patent
Huang et al.

(10) Patent No.: US 11,408,862 B2
(45) Date of Patent: Aug. 9, 2022

(54) ULTRASONIC EXTRACTION PERFORMANCE CHECKING DEVICE AND METHOD FOR ULTRASONIC EXTRACTOR FOR DETECTING AND ANALYZING CHEMICAL COMPOSITION OF CONSUMER PRODUCT

(71) Applicants: SHENZHEN TECHNOLOGY UNIVERSITY, Shenzhen (CN); TECHNOLOGY CENTER OF GUANGZHOU CUSTOMS, Guangzhou (CN)

(72) Inventors: Lina Huang, Shenzhen (CN); Lezhou Yi, Guangzhou (CN); Xiaoxia Mai, Guangzhou (CN); Huiling Qiu, Shenzhen (CN); Yong Tian, Guangzhou (CN); Chunnan Xu, Guangzhou (CN)

(73) Assignees: SHENZHEN TECHNOLOGY UNIVERSITY, Shenzhen (CN); TECHNOLOGY CENTER OF GUANGZHOU CUSTOMS, Guangzhou (CN)

( * ) Notice: Subject to any disclaimer, the term of this patent is extended or adjusted under 35 U.S.C. 154(b) by 298 days.

(21) Appl. No.: 16/498,686

(22) PCT Filed: Dec. 18, 2018

(86) PCT No.: PCT/CN2018/121667
§ 371 (c)(1),
(2) Date: Sep. 27, 2019

(87) PCT Pub. No.: WO2019/137163
PCT Pub. Date: Jul. 18, 2019

(65) Prior Publication Data
US 2020/0319145 A1 Oct. 8, 2020

(30) Foreign Application Priority Data

Aug. 29, 2018 (CN) .......................... 201810998212.1

(51) Int. Cl.
*G01N 29/30* (2006.01)
*G01N 29/22* (2006.01)
*G01N 33/00* (2006.01)

(52) U.S. Cl.
CPC .......... *G01N 29/30* (2013.01); *G01N 29/223* (2013.01); *G01N 33/00* (2013.01)

(58) Field of Classification Search
CPC ...... G01N 29/30; G01N 29/223; G01N 33/00; G01N 2001/4094; G01M 99/008
See application file for complete search history.

(56) References Cited

U.S. PATENT DOCUMENTS

| | | | | |
|---|---|---|---|---|
| 5,738,691 A | * | 4/1998 | Barker | ................ H01M 10/052 29/623.1 |
| 2010/0296976 A1 | * | 11/2010 | Hakari | ............... B01D 11/0496 422/128 |

* cited by examiner

*Primary Examiner* — Peter J Macchiarolo
*Assistant Examiner* — John M Royston
(74) *Attorney, Agent, or Firm* — Bayramoglu Law Offices LLC (57) ABSTRACT

An ultrasonic extraction performance checking device and method for an ultrasonic extractor for detecting and analyzing a chemical composition of a consumer product. The ultrasonic extraction performance checking device includes a hanging frame which is hung inside the ultrasonic extractor and matched with the ultrasonic extractor, and a hanging frame plane checking device which is detachably and vertically or horizontally placed in the hanging frame and clamped with an alloy foil. The alloy foil is surrounded by a tensioning fixture. The tensioning fixture causes the alloy foil to generate a surface tension of 5 to 15 N and to be (Continued)

tightened and fixed to the bottom surface of the hanging frame plane checking device.

10 Claims, 4 Drawing Sheets

Comparison Diagram of Horizontal Distributions of Sound Intensities under Two Modes

ULTRASONIC EXTRACTION PERFORMANCE CHECKING DEVICE AND METHOD FOR ULTRASONIC EXTRACTOR FOR DETECTING AND ANALYZING CHEMICAL COMPOSITION OF CONSUMER PRODUCT

CROSS REFERENCE TO THE RELATED APPLICATION

This application is the national phase entry of International Application No. PCT/CN2018/121667 filed on Dec. 18, 2018, which is based upon and claims priority to Chinese Patent Application No. CN201810998212.1, filed on Aug. 29, 2018, the entire contents of which are incorporated herein by reference.

TECHNICAL FIELD

The present invention relates to an ultrasonic extraction performance checking device and method for ultrasonic extractor for detecting and analyzing a chemical composition of a consumer product.

BACKGROUND

As a major toy producer and exporter of international consumer products, especially toy products, China produces nearly two-thirds toy product the world. The quality of toy products will directly affect China's international market. Toys with inferior quality and excessive pollutants will damage people's health and even threaten lives, especially for infants and young children. The detection of phthalate plasticizers is an important specific project. The traditional pretreatment methods for extraction of the phthalate plasticizer include Soxhlet extraction and solvent extraction, which are accompanied with long extraction time, low efficiency and difficulty in batch testing and have negative effects on testers and the environment because more solvents are used, and are thus not suitable for solid materials because of strict requirements on the size of an extraction material. Therefore, ultrasonic extraction is widely adopted by domestic and foreign enterprises and toy supervision departments in customs as a pretreatment method for rapidly and preliminarily screening the phthalate plasticizer, which has the advantages of short extraction time but high extraction efficiency, low solvent usage, and more suitable samples including solid materials. Since 2010, the former Guangdong Inspection and Quarantine Technology Center on behalf of China has led the drafting of ISO 8124-6 "Specific Phthalate Plasticizers for Toys and Children's Products" international standards. The latest version requires to check the performances of ultrasonic extractors for extraction, and those who have passed the checking can be used, thereby avoiding a case where the extraction is not complete, resulting in a false negative result.

Ultrasound extraction, also known as ultrasound assisted extraction or ultrasonic extraction, increases the molecular motion frequency and speed of substances and increases the solvent penetration by use of multi-stage effects such as a strong cavitation effect, a disturbance effect, a high acceleration, crushing and agitation actions caused by an ultrasound radiation pressure, thereby accelerating target components into a solvent, promoting the extraction and improving the extraction efficiency. The ultrasonic extraction technology has been applied more and more widely since its development. Compared with the traditional extraction technology, this novel extraction and separation technology has the advantages of high speed, safety, environmental friendliness, high efficiency, wide size range and low cost of suitable materials, and easy promotion. Therefore, the ultrasonic extraction technology has been widely used in the extraction of target organic matter content in consumer products such as textiles, toys, as well as electronic and electrical products.

The strength of the cavitation effect of ultrasonic extraction is related to the ultrasound frequency. The lower the frequency, the greater the cavitation bubbles, the higher the cavitation strength, whereas it is lower. Different frequency settings correspond to different uses. Commercially available ultrasonic generators are generally used for ultrasonic cleaners. Many of commercially available ultrasonic generators have a constant frequency, i.e., the frequency is not adjustable.

The sizes of bubbles produced by the existing commercially available ultrasonic generators can only satisfy cleaning use and are not suitable for ultrasonic extraction. The factors affecting the ultrasonic extraction efficiency include ultrasonic power, frequency, temperature, type of a solution medium and the like. In addition to the selection of the above parameter values, the sound field intensity and uniformity are of the most important influence factors. The conventional ultrasonic cleaner has the following problems: 1. the ultrasonic sound field intensity is not enough to satisfy the requirements of extraction strength; 2. the design and structural characteristics of an ultrasonic generator, such as the distribution of vibrators and the presence of standing waves in a cavity, result in uneven distribution of sound intensity, and it is not easy for samples which are placed in different positions to achieve consistent extraction efficiency when a large number of extracted samples are placed at one time; 3. due to the increase in the service time of the ultrasonic cleaner, the aging of core components and the damage of a bottom diaphragm, the ultrasonic intensity is easily attenuated over time, failing to ensure the extraction efficiency. Therefore, it is necessary to find a device for checking an ultrasonic extraction performance and a method for determining whether the parameter setting is reasonable or not, thereby (1) determining if this ultrasonic generator can be used for an extraction purpose during the working period; (2) checking an ultrasonic extractor to determine whether this ultrasonic extractor is working properly; (3) avoiding the difference in extraction levels caused by different positions of samples placed in an extraction basket during ultrasonic extraction, i.e., avoiding the positional "discrimination effect" during ultrasonic extraction; and (4) avoiding false negative detection results caused by blind zones, weak zones and unreasonable parameter settings of the ultrasonic sound field.

At present, methods for detecting cavitation of ultrasonic extractors include an o electrochemical method, TA method measurement, cavitation noise measurement, a staining method, a hydrophone method, a metal film method and the like. The staining method is cumbersome in operation and is not easy to quantify with digits. Values measured by the hydrophone method are instantaneous values, so the data has large fluctuation and poor reproducibility, which affects the detection accuracy of the performances of an ultrasonic cleaner. In addition, a measurement instrument used in the hydrophone method is expensive and high in detection cost. The problems of inconvenient operation and high detection cost also occur in the electrochemical method, the TA method measurement, and the cavitation noise measurement. An aluminum foil paper etching method is commonly used in the metal film method. The common aluminum foil corrosion degree evaluation method is to weigh an aluminum foil subjected to ultrasonic cavitation corrosion, and quantify the ultrasonic cavitation according to the change in the weight of the aluminum foil. However, the weighing method is greatly affected by the uneven thickness of the aluminum foil, and can only reflect a corrosion speed.

SUMMARY

An objective of the present invention is to provide an ultrasonic extraction performance checking device and method for ultrasonic extractor for detecting and analyzing a chemical composition of a consumer product, which are simple to operate, visual and easy to distinguish, and capable of detecting the performances of the ultrasonic extractor visually, such that the ultrasonic performances of the ultrasonic extractor for detecting and analyzing the chemical composition of the consumer product are easily determined, and the operation efficiency can be obviously improved.

The present invention is implemented by means of the following technical solution.

There is provided an ultrasonic extraction performance checking device for an ultrasonic extractor for detecting and analyzing a target chemical composition of a consumer product, wherein the ultrasonic extractor is configured to extract a target chemical composition in the consumer product; the ultrasonic extractor has an ultrasonic frequency of 20-45 kHz, and an ultrasonic power per unit area of 0.25-2.0 w/cm$^2$; the ultrasonic distribution uniformity and the ultrasonic field intensity make the ultrasonic extraction efficiency in the volume of a sample analyzed in any unit not lower than the extraction efficiency of the corresponding Soxhlet extraction; the ultrasonic extraction performance checking device is characterized by comprising a hanging frame which is hung inside the ultrasonic extractor, and a hanging frame plane checking device which is detachably and vertically or horizontally placed in the hanging frame and clamped with an alloy foil; the alloy foil is surrounded by a tensioning fixture which may be, for example, a spring or an elastic sheet; the tensioning fixture causes the alloy foil to generate a surface tension of 5 to 15 N and to be tightened and fixed to the bottom surface of the hanging frame plane checking device; the hanging frame comprises a cubic bottom frame, and buckles arranged on both sides of the upper end of the bottom frame and configured to fix and hang the hanging frame in the ultrasonic extractor, wherein a side frame is arranged on side surfaces around the cubic bottom frame, and configured to fix the hanging frame plane checking device that is vertically or horizontally placed and clamped with the alloy foil; the alloy foil is an empty alloy foil which may be printed with lattices (e.g., 1 cm×1 cm) suitable for bottom area of an extraction bottle or paved with transparent lattice paper having lattices (e.g., 1 cm×1 cm) suitable for bottom area of an extraction bottle; the bottom surface of the hanging frame is 10-50 mm from a bottom ultrasonic generation surface of the ultrasonic extractor; the parameters of the alloy foil are required to satisfy the following requirements: the aluminum content is 82% or more, the zinc content is 1%-10%, and the titanium content is 0.01%-0.1%; the tensile strength is 50-100 N/mm; the bursting strength is 150-200 KPa, and the thickness is 0.015-0.030 mm; the alloy foil is flat, smooth, free of wrinkles and free of small holes; the alloy foil has an area not greater than a cross-sectional area of the bottom surface of the hanging frame.

The chemical composition includes phthalate plasticizers, bisphenol A, polycyclic aromatic hydrocarbons, short-chain chlorinated paraffin, dimethyl fumarate, bromine-based flame retardants and phosphorus-based flame retardants.

In particular, the side frame is provided with buckles, and a distance between the buckles is freely adjustable in a range of 0.5-5 cm, such that the hanging frame plane checking device clamped with the alloy foil is fixed at different vertical heights or horizontal heights as required.

The alloy foil has an aluminum content of 82% or more, the zinc content of 1%-10%, and the titanium content of 0.01%-0.1%; the alloy foil of this specific formulation is easily crushed and eroded by ultrasonic waves having an ultrasonic length of 20-50 microns.

The tensile strength of the alloy foil is 50-100 N/mm$^2$; the bursting strength of the alloy foil is 150-200 Kpa; the bursting strength and the tensile strength are required to correspondingly satisfy the extraction rate requirement of more than 95% extraction of phthalate plasticizers in PVC, PU, ABS, PE and other materials.

The alloy foil is printed with lattices having a certain area or paved with transparent lattice paper having a certain area, wherein the lattices may averagely divide the alloy foil at a size of 1-5 cm. This size should simulate the placement conditions of different analytical extraction sample bottles in the hanging frame to determine the size and number of the lattices. By means of this design, a broken hole rate is calculated conveniently.

The alloy foil is placed according to the following method: the alloy foil is 10-50 mm from an ultrasonic generation surface of the ultrasonic extractor, and is horizontally more than 1 cm from the edge of the hanging frame. The vertical hanging design ensures that the tested alloy foil does not come into contact with an ultrasonic vibrator and a vibration surface, so as to avoid affecting the distribution and intensity of the ultrasonic field. In addition, the hanging height and the horizontal placement position cover the strongest area of the vertical distribution of the ultrasonic field intensity.

The present invention further provides an ultrasonic extraction performance checking method for an ultrasonic extractor for detecting and analyzing a chemical composition of a consumer product, where the ultrasonic extraction performance checking device for the ultrasonic extractor for detecting and analyzing the chemical composition of the consumer product is used, comprises the following steps:

1) tensioning and fixing an alloy foil on the bottom surface of a hanging frame plane checking device through a tensioning fixture; keeping the alloy foil flat; hanging a hanging frame inside the ultrasonic extractor; installing the hanging frame plane checking device clamped with the alloy foil at different horizontal positions and vertical heights, such that the alloy foil is perpendicularly more than 10-50 mm from a bottom ultrasonic generation surface of the ultrasonic extractor, and is horizontally more than 1 cm from the edge of the hanging frame; injecting a solvent to a normal use level of the ultrasonic extractor;

2) turning on the ultrasonic extractor and operating for 1-10 min, such that under an ultrasonic cavitation effect and other secondary effects, the alloy foil paper undergoes cavitation corrosion to form small holes; taking the alloy foil out, and directly observing printed lattices suitable for bottom area of extraction bottle or paved transparent lattice paper having lattices suitable for bottom area of the extraction bottle; observing the area and distribution conditions of corroded small holes; checking the breakage condition of the alloy foil to further evaluate the sound field coverage and intensities of the ultrasonic extractor at different horizontal positions and different vertical heights, wherein when a small hole greater than 1-5 mm in a one-dimensional direction appears on the alloy foil, it may be judged that this lattice has a broken hole; a through hole having a length greater than 1-5 mm in a lattice is taken as an effective broken lattice, which indicates that the ultrasonic extraction strength at this position is sufficient and this position may be used as an extraction position; this method can effectively evaluate the partial extraction efficiency of ultrasonic extractor.

When evaluating overall ultrasonic extraction sound field coverage performances, if the number of total effective broken lattices is less than 1/3 of the total number of lattices of the ultrasonic extractor, the ultrasonic extraction sound field coverage is weak; when a ratio of the total effective broken lattices is 1/3-2/3, it is indicated that the sound field coverage of the ultrasonic extractor is medium; when a ratio of the total effective broken lattices is greater than 2/3, it is indicated that the sound field coverage of the ultrasonic extractor is favorable and the parameter design is reasonable, such that the ultrasonic extractor may be used to ultrasonically extract samples in batch, and it is determined that the area where the ultrasonic extractor is located may be used as an extraction position.

The present invention has the following beneficial effects.

1. The present invention firstly proposed a method for quantitatively characterizing the extraction performances of an ultrasonic extractor by calculating the broken hole rate of lattices in an intuitive manner.

2. The present invention firstly proposed a device for evaluating partial and overall ultrasonic extraction performances using a special alloy foil, and a checking method.

3. The device and the method of the present invention are simple to operate, visual and easy to distinguish, and capable of detecting the performances of the ultrasonic extractor visually, such that the ultrasonic performances of the ultrasonic extractor for detecting and analyzing the chemical composition of the consumer product may be determined easily, and the operation efficiency may be obviously improved.

BRIEF DESCRIPTION OF THE DRAWINGS

in which, 1: service life of 5 years, 2: service life of 3 years, and 3: service life of 1 year.

in which 1: hanging frame, 2: alloy foil, 3: ultrasonic extractor for detecting and analyzing the chemical composition of the consumer product, and 4: water.

in which 2: alloy foil, 5: bottom frame, 6: buckle, and 7: side frame.

in which 2: alloy foil, 5: bottom frame, 6: buckle, and 7: side frame.

DETAILED DESCRIPTION OF THE EMBODIMENTS

The following content is intended to further describe the present invention, rather than limiting the present invention.

In order to investigate the necessity for ultrasonic performance checking, the energy in an ultrasonic generator cavity of the ultrasonic extractor for detecting analyzing the chemical composition of the consumer product is measured by a sound intensity meter or a sound pressure meter. The following experiments are carried out to primarily understand the energy distribution. It is found as follows: the design and structural characteristics of the ultrasonic generator, the service life of the ultrasonic generator, and the use mode of ultrasonic waves, as well as the presence of standing waves in the ultrasonic generator cavity itself, may result that weak zones or blind zones are present in the cavity or even the entire generator may not satisfy the extraction requirements. The detailed description is as follows.

Figure 1:
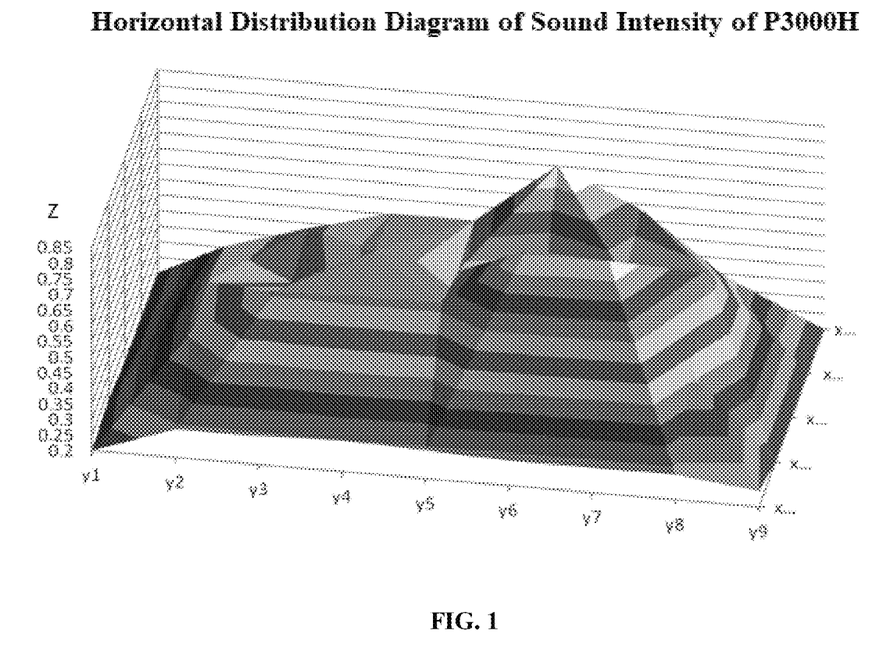
FIG. 1 is a schematic diagram showing the horizontal distribution of a sound field at a specific height in an ultrasonic cavity of an ultrasonic extractor for detecting and analyzing a chemical composition of a consumer product according to the present invention.

(1) Due to the design and structural characteristics of the ultrasonic generator, such as the distribution of vibrators and the presence of standing waves, the distribution of the sound intensity in the ultrasonic cavity is not completely uniform. FIG. 1 is a schematic diagram of testing the horizontal distribution of a sound field at a position, which is 30 mm from the bottom of the ultrasonic extractor, in the ultrasonic cavity of the ultrasonic extractor for detecting and analyzing the chemical composition of the consumer product by the sound intensity meter, wherein the Z axis refers to a measured sound intensity value.

Figure 2:
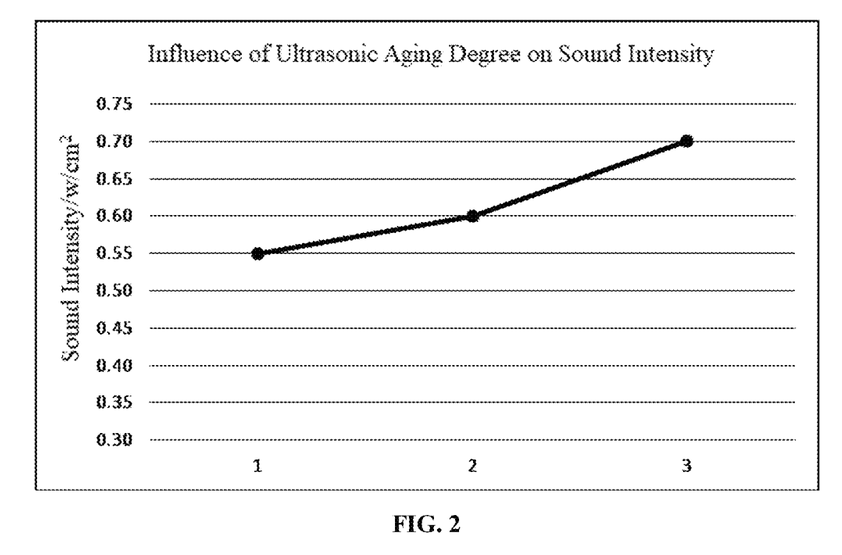
FIG. 2 is a diagram showing a relationship between the aging degree and the ultrasonic sound intensity of the ultrasonic extractor for detecting and analyzing the chemical composition of the consumer product according to the present invention.

(2) As the service life of the ultrasonic generator increases, the vibrators will be gradually aged, and the aging degree will affect the sound intensity. As the service life of the ultrasonic waves increases and components are aged, the sound intensity of ultrasonic waves will be reduced. The variation trend of the sound intensities in the ultrasonic generators of Elma's P300H with different service lives was investigated to understand the influences of the aging degree of the generator on the sound intensity. Three Elma P300H ultrasonic extractors with the service life of 5 years, the service life of 3 years and the service life of 1 year were selected to perform ultrasonic processing at the output energy of 80%. A sound intensity value of the center position of the ultrasonic wave, which is 30 mm from the bottom, is measured. The results are shown in FIG. 2.

Figure 3:
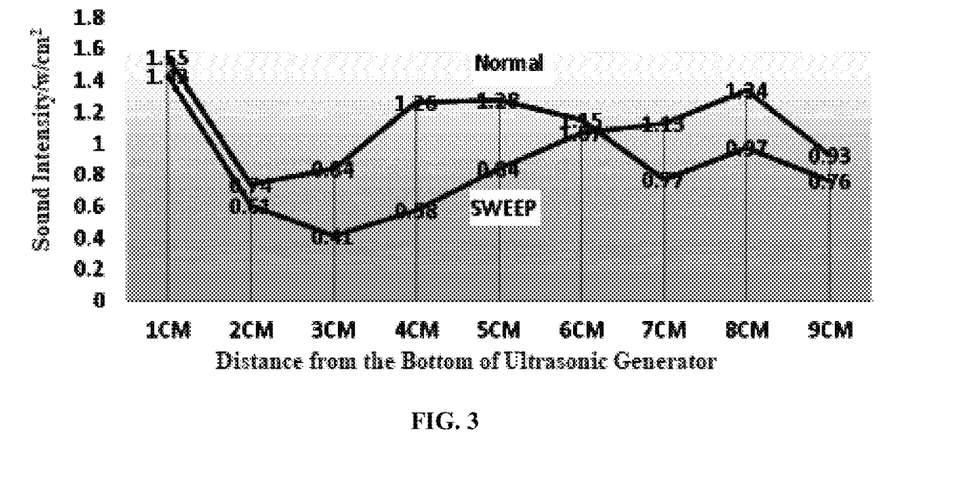
FIG. 3 shows the comparison of the sound intensity uniformity of ultrasonic waves in a vertical direction, and the investigation of the effects of two different ultrasonic modes on the sound intensity.
Figure 4:
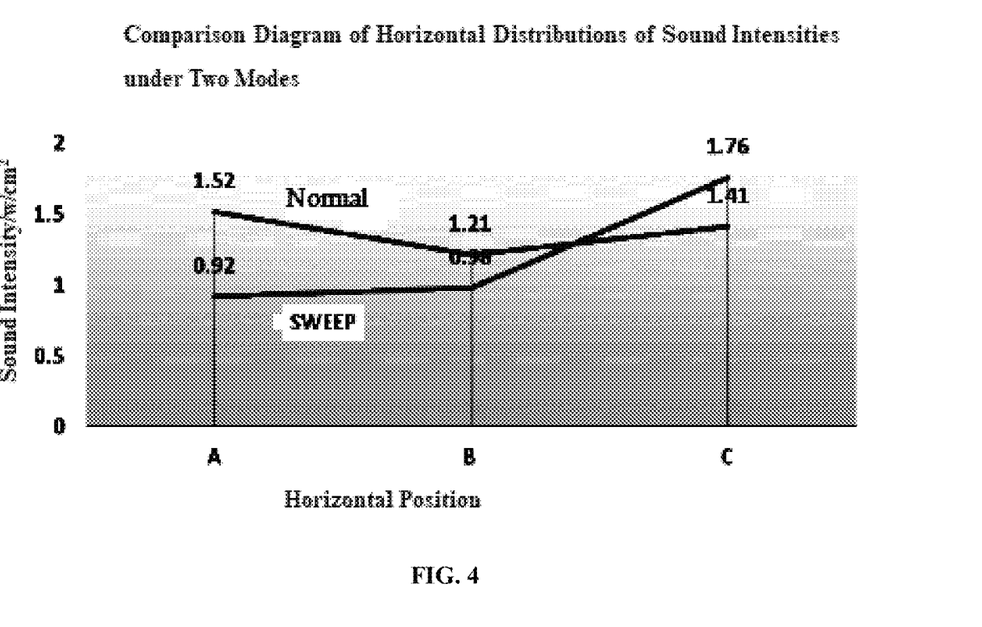
FIG. 4 shows the comparison of the sound intensity uniformity of ultrasonic waves in a horizontal direction, and the investigation of the effects of two different ultrasonic modes on the sound intensity.
Figure 5:
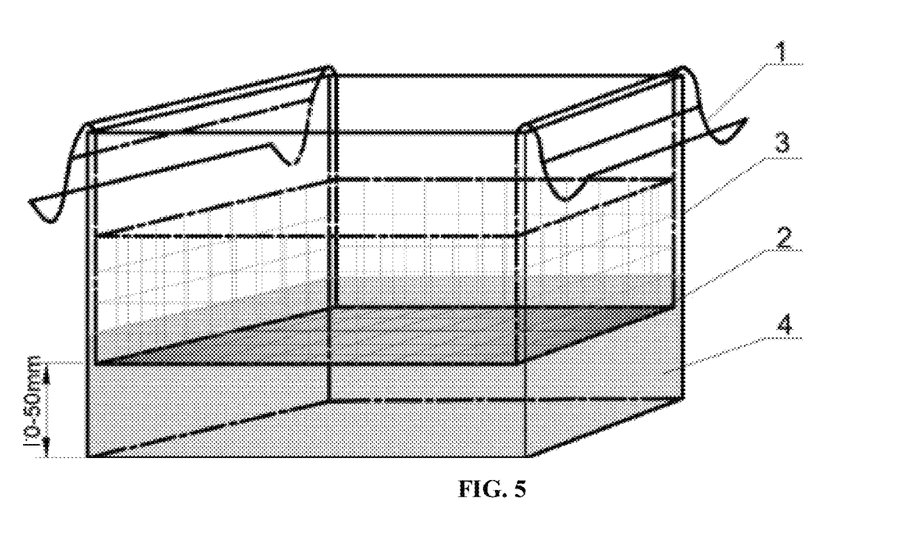
FIG. 5 is a schematic diagram showing a state in which a hanging frame plane checking device clamped with an alloy foil in an ultrasonic extraction performance checking device of the ultrasonic extractor for detecting and analyzing the chemical composition of the consumer product of the present invention is horizontally placed and used.
Figure 6:
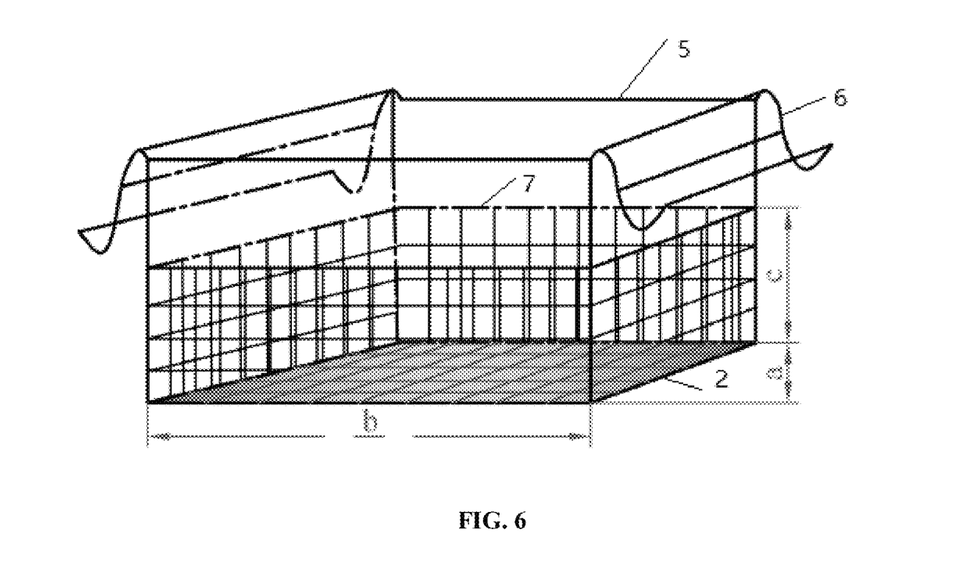
FIG. 6 is a schematic structural diagram of an ultrasonic extraction performance checking device of the ultrasonic extractor for detecting and analyzing the chemical composition of the consumer product (when the hanging frame plane checking device clamped with the alloy foil is placed horizontally on the bottom surface of the hanging frame)

(3) An Elma P300H ultrasonic cleaner was selected, wherein Normal and Sweep modes that are often used for extraction are selected. The Sweep mode is used to eliminate a standing wave effect and make the sound intensity in the ultrasonic waves more uniform. The power output of 80% in Normal and Sweep modes was investigated. In a unit of ¼ wavelength, the sound intensity values of three intermediate points (A, B, C) which are at different vertical heights of 1 cm-9 cm from the center of the cavity, divide the horizontal central axis of the cavity in four equal parts and are 30 mm high from the bottom of the cavity are tested. The uniformity of sound intensities of the ultrasonic extractor in the cavity in the vertical and horizontal directions are investigated. The results are as shown in FIG. 3 and FIG. 4.

As known from the above experiments, the design and structural characteristics of the ultrasonic generator of the ultrasonic extractor, the service life of the ultrasonic extractor, and the use mode of ultrasonic waves, as well as the presence of standing waves in the ultrasonic generator cavity itself and the like, may result that weak zones or blind zones are present in the cavity or even the entire generator may not satisfy the extraction requirements.

For example, in an ultrasonic extraction method of phthalate plasticizers in toys sample, plasticizers extraction is usually performed for 2-6 mm plastic micelles. It may be derived from the experimental results in combination with theoretical analysis that the ultrasonic frequency in a frequency range of 20-45 kHz is selected, the rated ultrasonic power per unit area is 0.25-2.0 w/cm.sup.2, and the uniformity in the ultrasonic distribution and a certain ultrasonic field intensity are ensured such that the ultrasonic extraction efficiency in the volume of a sample analyzed in any unit is not lower than the extraction efficiency of the corresponding Soxhlet extraction.

Figure 7:
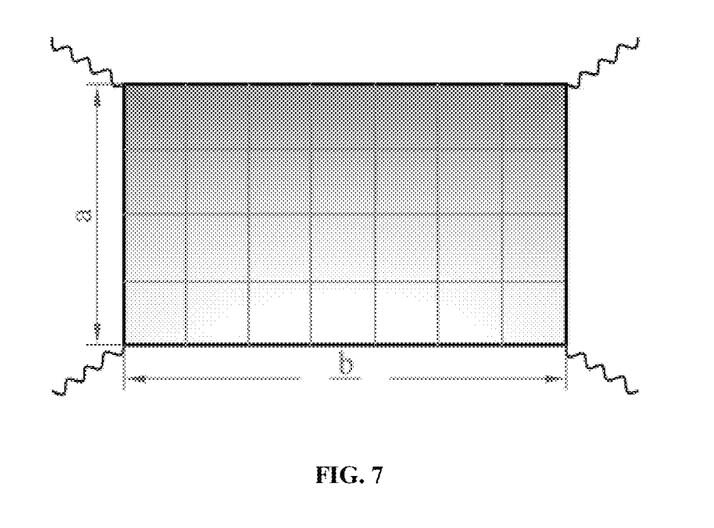
FIG. 7 is a schematic structural diagram of the alloy foil in FIG. 6.
Figure 8:
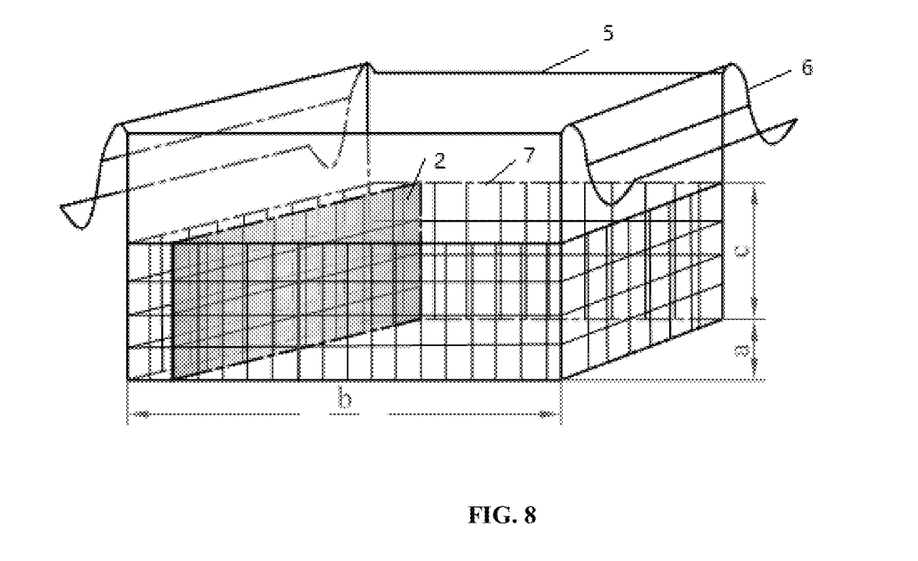
FIG. 8 is a schematic structural diagram of an ultrasonic extraction performance checking device of the ultrasonic extractor for detecting and analyzing the chemical composition of the consumer product (when the hanging frame plane checking device clamped with the alloy foil is placed vertically on the bottom surface of the hanging frame)

In order to check that the ultrasonic extraction efficiency of the ultrasonic extractor satisfies the requirements, an ultrasonic extraction performance checking device for an ultrasonic extractor for detecting and analyzing a chemical composition of a consumer product as shown in FIGS. 5-8 is used. The chemical composition is phthalate plasticizers. The ultrasonic extraction performance checking device comprises a hanging frame 1 which is hung inside the ultrasonic extractor 3 and matched with the ultrasonic extractor 3, and a hanging frame plane checking device which is detachably and vertically (see FIG. 8) or horizontally (see FIG. 6) placed in the hanging frame 1 and clamped with an alloy foil 2. As shown in FIG. 7, the alloy foil 2 is surrounded by a spring tensioning fixture. The spring tensioning fixture causes the alloy foil 2 to generate a surface tension of 5 to 15 N and to be tightened and fixed to the bottom surface of the hanging frame plane checking device. The hanging frame 1 comprises a cubic bottom frame 5, and buckles 6 arranged on both sides of the upper end of the bottom frame and configured to fix and hang the hanging frame in the ultrasonic extractor 3, wherein a side frame 7 is arranged on side surfaces around the cubic bottom frame 5, and configured to fix the hanging frame plane checking device that is vertically or horizontally placed and clamped with the alloy foil 2. As shown in FIG. 7, the alloy foil 2 is an empty alloy foil that is paved with transparent lattice paper having lattices of 5 cm×5 cm or printed with lattices of 5 cm×5 cm. The bottom surface of the hanging frame 1 is 10-50 mm from a bottom ultrasonic generation surface of the ultrasonic extractor 3. The parameters of the alloy foil are required to satisfy the following requirements: the aluminum content is 82% or more, the zinc content is 1%-10%, and the titanium content is 0.01%-0.1% (the alloy foil of this specific formulation is easily crushed and eroded by ultrasonic waves having an ultrasonic length of 20-50 microns); the tensile strength is 50-100 N/mm$^2$; the bursting strength is 150-200 KPa (the breaking resistance and the tensile strength are required to correspondingly satisfy the extraction rate requirement of more than 95% extraction of phthalate plasticizers in PVC, PU, ABS, PE and other materials), and the thickness is 0.015-0.030 mm; the alloy foil is flat, smooth, free of wrinkles and free of small holes; the alloy foil has an area not greater than a cross-sectional area of the bottom surface of the hanging frame.

In particular, the side frame is provided with buckles, and a distance between the buckles is 0.5-5 cm, such that the hanging frame plane checking device clamped with the alloy foil is fixed at different vertical heights or horizontal heights as required.

The alloy foil is paved with transparent lattice paper having square lattices or printed with lattices, wherein the lattices may averagely divide the alloy foil at a certain size. This size should simulate the placement conditions of different analytical extraction sample bottles in the hanging frame to determine the size and number of the lattices. By means of this design, a broken hole rate is calculated conveniently.

The alloy foil is placed according to the following method: the alloy foil is 10-50 mm from an ultrasonic generation surface of the ultrasonic extractor, and is horizontally more than 1 cm from the edge of the hanging frame. The vertical hanging design ensures that the tested alloy foil does not come into contact with an ultrasonic vibrator and a vibration surface, so as to avoid affecting the distribution and intensity of the ultrasonic field. The hanging height and the horizontal placement position cover the strongest area of the vertical distribution of the ultrasonic field strength.

The ultrasonic extraction performance checking method for the ultrasonic extractor for detecting and analyzing the chemical composition of the consumer product, where the ultrasonic extraction performance checking device for the ultrasonic extractor is used, comprises the following steps:

1) tensioning and fixing an alloy foil on the bottom surface of a hanging frame plane checking device through a spring tensioning fixture; keeping the alloy foil flat; hanging a hanging frame inside the ultrasonic extractor; installing the hanging frame plane checking device clamped with the alloy foil at different horizontal positions and vertical heights, such that the alloy foil is perpendicularly more than 10-50 mm from a bottom ultrasonic generation surface of the ultrasonic extractor, and is horizontally more than 1 cm from the edge of the hanging frame; injecting a solvent to a normal use level of the ultrasonic extractor;

2) turning on the ultrasonic extractor and operating for 2-5 min, such that under an ultrasonic cavitation effect and other secondary effects, the alloy foil paper undergoes cavitation corrosion to form small holes; taking the alloy foil out, and directly observing the alloy foil printed with lattices of 5 cm×5 cm, or paving the empty alloy foil with transparent lattice paper having lattices of 5 cm×5 cm, and observing the size and distribution conditions of the corroded small holes; checking the broken condition of the alloy foil to evaluate the sound field coverages and intensities of the ultrasonic extractor at different horizontal positions and different vertical heights. When a small hole greater than 1-5 mm in a one-dimensional direction appears on the alloy foil, it may be judged that this lattice has a broken hole. A through hole having a length greater than 1-5 mm in a lattice is taken as an effective broken lattice. The distribution conditions of the corroded small holes are observed to further evaluate the sound field coverage performance of entire ultrasonic extraction.

Three different ultrasonic extractors were checked by using the above method. The three ultrasonic extractors were used to extract a positive sample of the same phthalate plasticizer respectively, and the results are shown in Table 1. As can be seen from data in Table 1, the test results of the No. 1 and No. 2 ultrasonic extractors are close to a true value respectively, the test result of the No. 3 ultrasonic extractor is far less than the true value, and the value of |Z| is greater than 2. Therefore, the No. 3 ultrasonic extractor is not suitable for an extraction test of a phthalate plasticizer in a toy.

It is proved through experiments (see Table 1) that when the number of effective broken lattices of the alloy foil exceeds 2/3 of the number of lattices in a sample placement area, it is indicated that the performance state of the extractor is favorable, the parameter design is reasonable, and the test result is close to a true value, such that the extractor may be used for ultrasonically extracting samples in batch. When the number of total effective broken lattices is less than 1/3 of the total number of lattices in the sample placement area of the ultrasonic extractor, it is indicated that the ultrasonic extraction field intensity coverage is weak. When the ratio of the effective broken lattices is 1/3-2/3, it is indicated that the coverage of the ultrasonic extractor is medium.

TABLE 1

| Ultrasonic waves | Broken hole rate | Content of Di (2-Ethyl Hexyl) Phthalate (DEHP) in PVC plastic (mg/kg) | True value (mg/kg) | Z value |
| --- | --- | --- | --- | --- |
| 1 | 70% | 2317 | 2100. | 0.63 |
| 2 | 75% | 1836 | | −0.77 |
| 3 | 38% | 1107 | | −2.88 |

Remarks: the true value is an average value of positive samples of the phthalate plasticizer tested by 20 toy laboratories in China using an ultrasonic extraction method during the checking process of ISO 8124-6 standard methods. The Z value is a comparison of each test value with the average value. If the Z value is between −2 and 2, it is indicated that the test data does not deviate.

Embodiment 1

The performances of an ultrasonic extractor for testing phthalate plasticizers in a toy by the checking method of the present invention are checked as follows: the bottom of a bottom frame of a hanging frame of a HA 2050 ultrasonic cleaner is 46 cm×26 cm in size, wherein the length is 46 cm, and after subtracting 3 cm from the edges on both sides, can be divided into 8 lattices with one lattice of 5 cm; the width is 26 cm, and after subtracting 3 cm from the edges on both sides, can be divided into 4 lattices with one lattice of 5 cm, that is, the entire alloy foil may be divided into 32 lattices. It is observed in all 32 lattices that there are 28 lattices having broken holes greater than 3 mm, so the broken hole rate is 28/32×100%=87.5%. It is judged that this ultrasonic instrument can be used for extracting phthalate plasticizers.

What is claimed is:

1. An ultrasonic extraction performance checking device for an ultrasonic extractor for detecting and analyzing a chemical composition of a consumer product, wherein the ultrasonic extractor is configured to extract a target chemical composition in the consumer product; the ultrasonic extractor has an ultrasonic frequency of 20-45 kHz, and an ultrasonic power per unit area of 0.25-2.0 w/cm$^2$; the ultrasonic extraction performance checking device comprises a hanging frame hung inside the ultrasonic extractor, and a hanging frame plane checking device is placed detachably and vertically or horizontally in the hanging frame and clamped with an alloy foil; the alloy foil is surrounded by a tensioning fixture; the tensioning fixture causes the alloy foil to generate a surface tension of 5 to 15 N and to be tightened and fixed to a bottom surface of the hanging frame plane checking device; the hanging frame comprises a cubic bottom frame, and buckles arranged on both sides of the upper end of the bottom frame and configured to fix and hang the hanging frame in the ultrasonic extractor, wherein a side frame is arranged on side surfaces around the cubic bottom frame, and configured to fix the hanging frame plane checking device that is placed vertically or horizontally and clamped with the alloy foil; the alloy foil is an alloy foil, wherein the alloy foil is printed with lattices for a bottom area of an extraction bottle or paved with a transparent lattice paper having lattices for the bottom area of the extraction bottle; the bottom surface of the hanging frame is 10-50 mm from a bottom ultrasonic generation surface of the ultrasonic extractor; parameters of the alloy foil are required to satisfy the following requirements: an aluminum content is 82% or more, a zinc content is 1%-10%, and a titanium content is 0.01%-0.1%; a tensile strength is 50-100 N/mm$^2$; the bursting strength is 150-200 KPa, and a thickness is 0.015-0.030 mm; the alloy foil is flat, smooth, free of wrinkles and free of holes; the alloy foil has an area not greater than a cross-sectional area of the bottom surface of the hanging frame.

2. The ultrasonic extraction performance checking device for the ultrasonic extractor for detecting and analyzing the chemical composition of the consumer product according to claim 1, wherein the tensioning fixture is a spring or an elastic sheet.

3. The ultrasonic extraction performance checking device for the ultrasonic extractor for detecting and analyzing the chemical composition of the consumer product according to claim 1, wherein the side frame is provided with buckles, and a distance between the buckles is 0.5-5 cm.

4. The ultrasonic extraction performance checking device for the ultrasonic extractor for detecting and analyzing the chemical composition of the consumer product according to claim 1, wherein the chemical composition is selected from the group consisting of more than one of phthalate plasticizers, bisphenol A, polycyclic aromatic hydrocarbons, short-chain chlorinated paraffin, dimethyl fumarate, bromine-based flame retardants and phosphorus-based flame retardants.

5. An ultrasonic extraction performance checking method for an ultrasonic extractor for detecting and analyzing a chemical composition of a consumer product using the ultrasonic extraction performance checking device for the ultrasonic extractor for detecting and analyzing the chemical composition of the consumer product according to claim 1, comprising the following steps:
 1) tensioning and fixing the alloy foil on the bottom surface of the hanging frame plane checking device through the tensioning fixture; keeping the alloy foil flat; hanging a hanging frame inside the ultrasonic extractor; installing the hanging frame plane checking device clamped with the alloy foil at different horizontal positions and vertical heights, such that the alloy foil is perpendicularly more than 10-50 mm from a bottom ultrasonic generation surface of the ultrasonic extractor, and is horizontally more than 1 cm from the edge of the hanging frame; injecting a solvent to a normal use level of the ultrasonic extractor;

2) turning on the ultrasonic extractor and operating for 1-10 min, such that under an ultrasonic cavitation effect and other secondary effects, the alloy foil paper undergoes cavitation corrosion to form holes; taking the alloy foil out, and directly observing printed lattices for a bottom area of an extraction bottle or paved transparent lattice paper having lattices for the bottom area of the extraction bottle; observing the area and distribution conditions of corroded holes; checking the breakage condition of the alloy foil to further evaluate the sound field coverage and intensities of the ultrasonic extractor at different horizontal positions and different vertical heights, wherein when a hole greater than 1-5 mm in a one-dimensional direction appears on the alloy foil, it may be judged that this lattice is a broken hole; a through hole having a length greater than 1-5 mm in a lattice is taken as an effective broken lattice, which indicates that the ultrasonic extraction strength at this position is sufficient and this position may be used as an extraction position;

when evaluating overall ultrasonic extraction sound field coverage performances, when the number of total effective broken lattices is less than 1/3 of the total number of lattices of the ultrasonic extractor, it is indicated that the ultrasonic extraction field intensity coverage is weak; when a ratio of the total effective broken lattices is 1/3-2/3, it is indicated that the coverage of the ultrasonic extractor is medium; when a ratio of the total effective broken lattices is greater than 2/3, it is indicated that the sound field coverage of the ultrasonic extractor is favorable and the parameter design is reasonable, such that the ultrasonic extractor may be used to ultrasonically extract samples in batch, and it is determined that the area where the ultrasonic extractor is located may be used as an extraction position.

6. The ultrasonic extraction performance checking device for the ultrasonic extractor for detecting and analyzing the chemical composition of the consumer product according to claim 3, wherein the tensioning fixture is a spring or an elastic sheet.

7. The ultrasonic extraction performance checking device for the ultrasonic extractor for detecting and analyzing the chemical composition of the consumer product according to claim 4, wherein the tensioning fixture is a spring or an elastic sheet.

8. The ultrasonic extraction performance checking method for an ultrasonic extractor for detecting and analyzing a chemical composition of a consumer product, according to claim 5, wherein the tensioning fixture is a spring or an elastic sheet.

9. The ultrasonic extraction performance checking method for an ultrasonic extractor for detecting and analyzing a chemical composition of a consumer product, according to claim 5, wherein the side frame is provided with buckles, and a distance between the buckles is 0.5-5 cm.

10. The ultrasonic extraction performance checking method for an ultrasonic extractor for detecting and analyzing a chemical composition of a consumer product, according to claim 5, wherein the chemical composition is selected from the group consisting of more than one of phthalate plasticizers, bisphenol A, polycyclic aromatic hydrocarbons, short-chain chlorinated paraffin, dimethyl fumarate, bromine-based flame retardants and phosphorus-based flame retardants.

* * * * *